(12) United States Patent
Echt et al.

(10) Patent No.: US 7,184,830 B2
(45) Date of Patent: Feb. 27, 2007

(54) METHODS AND SYSTEMS FOR TREATING ARRHYTHMIAS USING A COMBINATION OF VIBRATIONAL AND ELECTRICAL ENERGY

(75) Inventors: Debra S. Echt, Woodside, CA (US); Axel F. Brisken, Fremont, CA (US); Richard E. Riley, Palo Alto, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 256 days.

(21) Appl. No.: 10/869,242

(22) Filed: Jun. 15, 2004

(65) Prior Publication Data

US 2005/0043762 A1     Feb. 24, 2005

Related U.S. Application Data

(60) Provisional application No. 60/496,179, filed on Aug. 18, 2003.

(51) Int. Cl.
*A61N 1/18* (2006.01)

(52) U.S. Cl. .............. 607/3; 607/2; 607/4; 607/5; 607/119; 607/122; 607/129; 601/46

(58) Field of Classification Search ........... 607/2–5, 607/119, 122, 129; 601/46
See application file for complete search history.

(56) References Cited

U.S. PATENT DOCUMENTS

| | | | |
|---|---|---|---|
| 4,265,228 A * | 5/1981 | Zoll | 601/108 |
| 4,651,716 A | 3/1987 | Forester et al. | |
| 5,165,403 A | 11/1992 | Mehra | |
| 5,292,338 A | 3/1994 | Bardy | |
| 5,433,731 A | 7/1995 | Hoegnelid et al. | |
| 5,800,464 A | 9/1998 | Kieval | |
| 5,871,506 A | 2/1999 | Mower | |
| 5,935,158 A * | 8/1999 | Holmstrom et al. | 607/116 |
| 6,110,098 A | 8/2000 | Renirie et al. | |
| 6,233,484 B1 | 5/2001 | Ben-Haim et al. | |
| 6,330,475 B1 | 12/2001 | Renirie et al. | |

(Continued)

FOREIGN PATENT DOCUMENTS

WO    WO 99/061058    12/1999

(Continued)

OTHER PUBLICATIONS

Bardy et al., "The totally subcutaneous ICD system (The S-ICD)," PACE, 2002; 24,578.

(Continued)

*Primary Examiner*—Robert E. Pezzuto
*Assistant Examiner*—Deborah Malamud
(74) *Attorney, Agent, or Firm*—Townsend and Townsend and Crew LLP

(57) ABSTRACT

Methods and apparatus for cardiac pacing, cardioversion and defibrillation rely on delivering ultrasonic or other vibrational energy in combination with electrical energy to the heart, usually after the onset of an arrhythmia. A vibrational transducer and suitable electrical contacts may be combined in a single housing or distributed among various housings, and will usually be implantable so that the vibrational transducer can be directed at a target portion of the heart. Alternatively, external systems comprising the vibrational transducer and electrical contacts are also described.

62 Claims, 13 Drawing Sheets

U.S. PATENT DOCUMENTS

| | | |
|---|---|---|
| 6,408,205 B1 | 6/2002 | Renirie et al. |
| 6,439,236 B1 | 8/2002 | Porter et al. |
| 2003/0069625 A1* | 4/2003 | Ley et al. .................. 607/122 |

FOREIGN PATENT DOCUMENTS

| | | |
|---|---|---|
| WO | WO 03/070323 | 8/2003 |

OTHER PUBLICATIONS

Camm et al., "Nonpharmaceutical treatment of atrial fibrillation. In Atrial Fibrillation. Facts from Yesterday—Ideas for tomorrow," Futura Publishing Company, Inc., Armonk, NY, 1994.

Dalecki et al., "Thresholds for premature ventricular contractions in frog hearts exposed to lithotripter fields," *Ultrasound in Med. & Biol.* 1991; 17:341-346.

Dalecki et al., "Effects of pulsed ultrasound on the frog heart: I," Thresholds for changes in cardiac rhythm and aortic pressure, *Ultrasound in Med. & Biol.* 1993; 19:385-390.

Dalecki et al., "Effects of pulsed ultrasound on the frog heart: II. An investigation of heating as a potential mechanism," *Ultrasound in Med. & Biol.* 1993; 19:391-398.

Ellenbogen et al., "Detection and management of an implantable cardioverter defibrillator lead failure," *JACC.* 2003;41:73-80.

Feldman et al., "Comparison of medical therapy, resynchronization and defibrillation thetapies in heart failure trial (COMPANION)," Presented at ACC 2003 Late Breaking Clinical Trials.

Franz, "Mechano-electrical feedback in ventricular myocardium" *Cardiovascular Research.* 1996; 32:15-24.

Gibbons, "ACC/AHA/NASPE 2002 guideline update for implantation of cardiac pacemakers and antiarrhythmia devices: Summary Article, A report of the American College of Cardiology/American Heart Association Task Force on Practice Guidelines," (*ACC/AHA/ NASPE Committee to Update the 1998 Pacemaker Guidelines*). Circulation. 2002; 106:2145-2161.

Hu et al., "Stretch-activated ion channels in the heart," *J. Mol. Cell Cardiol.* 1997; 29:1511-1523.

Kohl et al, "Stretch-induced changes in heart rate and rhythm: clinical observations, experiments and mathematical models," *Progress in Biophysics & Molecular Biology.* 1999; 71:91-138.

Kohl et al., "Sudden cardiac death by Commatio cordis: role of mechano-electrical feedback," *Cardiovascular Research.* 2001; 50:280-289.

Lee et al., "Effect of implantable defibrillators of arrhythmic events and mortality in the multicenter unsustained tachycardia trial," Circulation. 2002; 106:233-238.

Moss et al., "Prophylactic implantation of a defibrillator in patients with myocardial infarction and reduced ejection fraction," *N Engl J Med.* 2002; 346:877-933.

Niehaus et al., "Non-contact cardiac stimulation with focused ultrasound pulses," *PACE* 2003: 26:1023.

Nolte et al., "Mechanically induced ventricular extrasystoles in the isolated perfused guinea-pig heart," *Arzneim.-Forsch/Drug Research.* 1987; 37(11): 1025-1029.

Reiter, "Effects of mechano-electrical feedback: potential arrhythmogenic influence in patients with congestive heart failure," *Cardiovascular Research.* 1996; 32:44-51.

Smailys et al., "Investigation of the possibilities of cardiac defibrillation by ultrasound," *Resuscitation.* 1981; 9:233-242.

Tacker, "Fibrillation causes and criteria for defibrillation. In *Defibrillation of the heart*," Tacker, WA, ed. Mosby-Year Book, Inc., St. Louis, Missouri, 1994.

The Antiarrhythmics Versus Implantable Defibrillators (AVID) Investigators: A comparison of antiarrhythmic drug therapy with implantable defibrillators in patients resuscitated from near fatal ventricular arrhythmias, *N Engl J Med* 1997;337: 1576-1583.

* cited by examiner

METHODS AND SYSTEMS FOR TREATING ARRHYTHMIAS USING A COMBINATION OF VIBRATIONAL AND ELECTRICAL ENERGY

CROSS-REFERENCES TO RELATED APPLICATIONS

The present application claims priority from U.S. Patent Application Ser. No. 60/496,179, filed Aug. 18, 2003, the full disclosure of which is incorporated herein by reference.

The disclosure of the present application is also related to the following applications being filed on the same day as the present application: U.S. patent Ser. No. 10/869,776; U.S. patent application Ser. No. 10/869,631; and U.S. patent application Ser. No. 10/869,705, the full disclosures of which are incorporated herein by reference.

BACKGROUND OF THE INVENTION

1. Field of the Invention

The present invention relates generally to medical devices and treatment methods. More particularly, the present invention relates to methods and apparatus for treating cardiac arrhythmias with vibrational energy.

Cardiac arrhythmias, including ventricular tachycardias and ventricular fibrillation, are a leading cause of morbidity and death in Western societies. A very successful technique for treating such arrhythmias is generally referred to as "ventricular cardioversion and defibrillation," where electrical energy is applied across the chest to synchronize cardiac rhythm. The use of external cardioversion and defibrillation equipment, i.e. where electrode paddles are placed externally on the chest and where relatively high electrical energy is applied, has been very effective, but of course requires the availability of both the equipment and an operator capable of using the equipment. More recently, implantable cardioverter defibrillator (ICD) devices have come into use, which are programmed to automatically intervene after the onset of an arrhythmia. ICD's stabilize the cardiac rhythm by delivering cardioversion, defibrillation, and pacing therapies as needed. Such ICD's have been shown to improve survival and have become the standard of therapy in patients at risk.

ICD's, however, do suffer from certain disadvantages. At present, ICD designs require one or more electrical leads to be implanted on or within the heart in order to provide pacing, cardioversion and defibrillation energy. Such lead placement requires skilled personnel and subjects the patient to radiation during the implantation procedure. The implanted leads are subject to failure and may cause cardiac perforation, thrombo-occlusion, and infection. Lead failure due to fracture or insulation break has been reported to occur in a significant fraction of the patient population after several years. In contrast, implanted leads used for bradycardia pacing have better reliability than ICD leads due to reduced electrical energy carrying requirements. It would be desirable to be able to use pacing leads, carrying less energy, to defibrillate patients and improve lead reliability. Present ICD's also require a relatively long time to charge capacitors, typically from 10–15 seconds, potentially delaying treatment after a potentially lethal arrhythmia is detected. Delay in treatment also requires higher energy delivery to be successful. Moreover, many patients who have received ICD's find that the electric shocks are painful, and the unpredictable nature of the ICD firing can cause anxiety and fear.

Atrial fibrillation is another form of cardiac arrhythmia and is characterized by rapid and disorganized electrical activity in both the left and right atria of the heart. Atrial fibrillation causes absence of atrial contraction and often atrial enlargement. Although not directly lethal, atrial fibrillation is associated with thrombus formation in the atrial appendages and has the potential for causing thrombolic stroke. The lack of coordinated atrial contraction can reduce cardiac output which can exacerbate other heart conditions. Patients in atrial fibrillation may experience heart failure, chest pain, fatigue, light headedness, and shortness of breath. The rapid and irregular heartbeat and palpitations associated with atrial fibrillation can be very distressing to patients. Thus, while atrial fibrillation is not directly fatal, it can be very distressing to patients and has a potential for increasing mortality from other conditions.

Atrial fibrillation may be controlled using the same techniques applied to ventricular arrhythmias, including both external defibrillators and ICD devices. The shortcomings of both these approaches discussed above, however, are even more of a concern for patients suffering from atrial fibrillation since patients are conscious and alert. Moreover, atrial fibrillation events often occur more frequently than ventricular arrhythmias, and patients are often unwilling to tolerate the pain associated with either external defibrillation or the use of ICD devices on such a frequent basis.

For these reasons, it would be desirable to provide improved methods and devices for the treatment of cardiac arrhythmias, including both ventricular arrhythmias and atrial arrhythmias. In particular, it would be desirable to provide such methods and systems for reducing the level of electrical energy required in order to achieve defibrillation and thus reduce the associated pain and shock. Particularly, it would be desirable if such methods and systems could be applied to both external defibrillation and the use of ICD devices. At least some of these objectives will be met by the inventions described below.

2. Description of the Background Art

Patents describing the treatment of arrhythmias using mechanical shock therapy include U.S. Pat. Nos. 6,408,205; 6,330,475; 6,110,098; and 5,433,731. See also U.S. Pat. Nos. 6,539,262; 6,439,236; 6,233,484; 5,800,464; 5,871,506; 5,292,338; 5,165,403; and 4,651,716, as well as WO 03/070323 and WO 99/61058. Medical publications discussing the effects of ultrasound energy and/or mechanical action on the heart include:

The Antiarrhythmics Versus Implantable Defibrillators (AVID) Investigators: A comparison of antiarrhythmic drug therapy with implantable defibrillators in patients resuscitated from near fatal ventricular arrhythmias. *N Engl J Med* 1997; 337: 1576–1583.

Bardy G H, Cappato R., Smith W M, Hood M, Rissmann W J, Gropper C M, Ostroff H. The totally subcutaneous ICD system (The S-ICD). PACE. 2002; 24, 578.

Camm A J, Murgatroyd F D. Nonpharmaceutical treatment of atrial fibrillation. In Atrial Fibrillation. Facts from Yesterday—Ideas for Tomorrow. Futura Publishing Company, Inc., Armonk, N.Y., 1994.

Dalecki D, Keller B B, Raeman C H, Carstensen E L. Effects of pulsed ultrasound on the frog heart: I. Thresholds for changes in cardiac rhythm and aortic pressure. *Ultrasound in Med. & Biol.* 1993; 19:385–390.

Dalecki D, Keller B B, Carstensen E L, Neel D S, Palladino J L, Noordergraaf A. Thresholds for premature ventricular contractions in frog hearts exposed to lithotripter fields. *Ultrasound in Med. & Biol.* 1991; 17:341–346.

Dalecki D, Raeman C H, Carstensen E L. Effects of pulsed ultrasound on the frog heart: II. An investigation of heating as a potential mechanism. *Ultrasound in Med. & Biol.* 1993; 19:391–398.

Ellenbogen K A, Wood M A, Shepard R K, Clemo H F, Vaughn T, Holloman K, Dow M, Leffler J, Abeyratne A, Verness D. Detection and management of an implantable cardioverter defibrillator lead failure. *JACC.* 2003; 41:73–80.

Feldman A and Bristow M. Comparison of medical therapy, resynchronization and defibrillation therapies in heart failure trial (COMPANION). Presented at ACC 2003 Late Breaking Clinical Trials.

Franz M R. Mechano-electrical feedback in ventricular myocardium. *Cardiovascular Research.* 1996; 32:15–24.

Gibbons R J, Antman E M, Alpert J S, Gregoratos G, Hiratzka L F, Faxon D P, Jacobs A K, Fuster V, Smith S C Jr. ACC/AHA/NASPE 2002 guideline update for implantation of cardiac pacemakers and antiarrhythmia devices: a report of the American College of Cardiology/American Heart Association Task Force on Practice Guidelines (*ACC/AHA/NASPE Committee to Update the 1998 Pacemaker Guidelines*). Circulation. 2002; 106: 2145–2161.

Hu H, Sachs F. Stretch-activated ion channels in the heart. *J Mol. Cell Cardiol.* 1997; 29:1511–1523.

Kohl P, Hunter P, Noble D. Stretch-induced changes in heart rate and rhythm: clinical observations, experiments and mathematical models. *Progress in Biophysics & Molecular Biology.* 1999; 71:91–138.

Kohl P, Nesbitt A D, Cooper P J, Lei M. Sudden cardiac death by Commotio cordis: role of mechano-electrical feedback. *Cardiovascular Research.* 2001; 50:280–289.

Kohl P and Ravens U. Cardiac mechano-electric feedback: past, present, and prospect, Prog. Biophys. Mol. Biol. 2003; 82:3–11.

Lee K L, Hafley G, Fisher J D, Gold M R, Prystowsky E N, Talajic M, Josephson M E, Packer D L, Buxton A E. Effect of implantable defibrillators of arrhythmic events and mortality in the multicenter unsustained tachycardia trial. Circulation. 2002; 106:233–238.

Moss A J, Zareba W, Hall W J, Klein H, Wilber D J, Cannom D S, Daubert J P, Higgins S L, Brown M W, Andrews M L. Prophylactic implantation of a defibrillator in patients with myocardial infarction and reduced ejection fraction. *N Engl J Med.* 2002; 346:877–933.

Niehaus M, Pirr J, De Sousa M, Houben R, Korte T, Eick O J. Non-contact cardiac stimulation with focused ultrasound pulses. *PACE* 2003: 26:1023.

Nolte S, Doring J H, Frey A. Mechanically induced ventricular extrasystoles in the isolated perfused guinea-pig heart. *Arzneim.-Forsch/Drug Research.* 1987; 37(11): 1025–1029.

Reiter M J. Effects of mechano-electrical feedback: potential arrhythmogenic influence in patients with congestive heart failure. *Cardiovascular Research.* 1996; 32:44–51.

Smailys A, Dulevicius Z, Muckus K, Dauksa K. Investigation of the possibilities of cardiac defibrillation by ultrasound. *Resuscitation.* 1981; 9:233–242.

Tacker, W A. Fibrillation causes and criteria for defibrillation. In *Defibrillation of the heart.* Tacker, W A, ed. Mosby-Year Book, Inc., St. Louis, Mo., 1994.

BRIEF SUMMARY OF THE INVENTION

The present invention provides methods and systems for treating cardiac arrhythmias, including both ventricular and atrial arrhythmias, by the combined delivery of both electrical energy and vibrational energy to the heart. It is presently believed that delivery of electrical energy and vibrational energy may induce a variety of mechanisms by which the same or different mechano-sensitive ion channels are affected to terminate the arrhythmia. When delivered simultaneously, the electrical and vibrational energies may combine to increase the effect on particular ion channels or to affect different ion channels in different ways. Thus, the improvement with the combined therapy may result from a greater effect on particular myocardial cells than achieved with either therapy alone or alternatively by affecting a greater number of myocardial cells than could be achieved with either therapy alone, at least at lower energy levels. Thus, the present invention may achieve the successful termination of arrhythmias using lower electrical and/or vibrational energy levels or may alternatively use the same energy level(s) with a greater efficiency. The ability to use lower energy levels allows for a number of system improvements, including more efficient use of batteries, greater margins of safety for treatment, as well as a reduction in pain. In addition, the methods and systems of the present invention may provide electrical and/or vibrational energy for pacing of selected heart chambers. Furthermore, pace termination of tachyarrhythmias, using programmed trains of pacing stimuli at prespecified intervals and durations, rather than higher energy electrical shock termination, may be enhanced using electrical and/or vibrational energy.

Thus, in a first aspect of the present invention, methods for stabilizing cardiac arrhythmias comprise delivering controlled vibrational energy from a vibrational transducer to the heart and, concurrently and/or successively or alternatively, delivering electrical energy to the heart, where the vibrational energy and/or electrical energy are delivered under conditions which terminate the arrhythmia. The vibrational energy and electrical energy may be delivered by either implanted device(s) or external device(s).

The location at which the devices are implanted and/or externally engaged against the patient's skin will be determined at least in part based on the particular therapy being applied. For example, for the treatment of ventricular arrhythmias including both ventricular fibrillation and ventricular tachycardia, the device may be implanted at least partially under the patient's ribs, at least partially in a gap between the patient's ribs, at least partially over the patient's ribs and/or sternum, or in an abdominal region of the patient. The precise location will be chosen to optimize delivery of the energy, particularly the vibrational energy, to the ventricular aspect of the heart. The electrical energy will usually be delivered by implantable leads containing electrodes extending from the implantable housing which contains the vibrational transducer and associated control and power circuitry. The implantable leads may be placed transvenously to one or more of the heart's atria or ventricles. The implantable leads may be placed subcutaneously. Alternatively, the electrical energy could be delivered in part from subcutaneous electrodes or from electrodes on the implantable housing.

Externally delivered vibrational energy and electrical energy for the treatment of ventricular arrhythmias will typically be accomplished by apparatus engaged against the patient's chest. Electrical contacts may be generally conventional defibrillation electrode pads or paddles. The vibrational transducer(s) will be located generally over the ventricular region of the heart along a path which permits penetration of the vibrational energy to the ventricle(s).

Alternatively, the vibrational transducer(s) may be located within the defibrillation pads or paddles.

For the treatment of atrial arrhythmias, vibrational energy may be directed from the anterior chest or alternatively the posterior chest. Thus, the apparatus for delivering the vibrational energy may be implanted at least partially either over the ribs and/or sternum or in a gap between the ribs or beneath the ribs in the anterior chest, or over the ribs in the posterior chest.

The vibrational energy will be delivered under conditions which synergize with the electrical energy to either reduce the electrical energy required to terminate the arrhythmia and/or to enhance the effectiveness of the termination of the arrhythmia. Preferred characteristics for the delivery of the vibrational energy are set forth below. The electrical energy may be delivered at conventional power levels and under conventional control algorithms as are presently employed with either external defibrillators or implantable cardioverter defibrillator (ICD) devices. Advantageously, however, the delivery of vibrational energy according to the present invention will usually permit lowering of the electrical energy delivered through the electrical contacts to the heart. Thus, the pain and inconvenience of both external and internal defibrillation associated with electrical defibrillators may be lessened or eliminated entirely.

Alternatively or optionally, vibrational energy will be delivered to terminate certain specific arrhythmias detected, while electrical energy will be delivered to terminate other specific arrhythmias detected. As an example, one energy source may be used to accomplish pacing therapy, while the other may be used to accomplish defibrillation therapy. This would be advantageous when an arrhythmia is more responsive to one energy source than the other.

Methods according to the present invention will usually further comprise detecting an onset of an arrhythmia, particularly when delivering the vibrational and/or electrical energy using an implanted device. Particularly for the treatment of ventricular arrhythmias, the automatic delivery of both the controlled vibrational energy and the electrical energy in automatic response to detection of the arrhythmia is an advantage. Alternatively, particularly in the case of the treatment of atrial arrhythmias, it may be possible to initiate the delivery of controlled vibrational energy and/or electrical energy manually, using other implanted or external devices. For example, implantable devices could be programmed to permit initiation of therapy by the patient or another individual using an external wand or similar device which can transcutaneously control the implanted circuitry.

Systems according to the present invention for stabilizing cardiac arrhythmias are comprised of a vibrational transducer adapted to deliver vibrational energy to the heart, electrical contacts adapted to deliver electrical energy to the heart, and control circuitry for delivering at least one of the vibrational energy and the electrical energy to the heart under selected conditions. As described above in connection with the methods of the present invention, the vibrational transducer and/or the electrical contacts may be implantable or alternatively may be adapted to externally engage the patient's skin. For implantable devices, the vibrational transducer will operate under the conditions described in more detail below. The electrical energy will be delivered under conditions generally utilized for implantable cardioverter devices or preferably, at power levels lower than those conventionally employed for such implantable defibrillators. Particular electrical energy levels are set forth in more detail below.

For the external systems of the present invention, the vibrational energy levels are generally set forth below. The electrical energy may be delivered under conditions generally as used in conventional external defibrillators, but will more preferably be delivered at energy and power levels much lower than those employed by conventional external defibrillators. Particular electrical power levels are set forth below.

The control circuitry of the systems of the present invention will optionally include systems for detecting an onset of an arrhythmia and for automatically activating and synchronizing the delivery of vibrational energy and/or electrical energy in response to such detection. Alternatively, the control circuitry may be configured to allow manual activating and synchronizing the delivery of either or both the vibrational and electrical energies.

The systems will further be configured to control the order and duration of delivery of both the vibrational energy and the electrical energy. Usually, the vibrational energy and electrical energy will be delivered at least partly simultaneously. Under particular circumstances, however, it may be advantageous to commence the delivery of the vibrational energy prior to the delivery of the electrical energy or, alternatively, initiate the delivery of the electrical energy prior to the delivery of the vibrational energy.

The systems may be configured in a variety of ways. Usually, the vibrational transducer, the electrical contacts, and the control circuitry will be packaged in or as part of a common housing. Alternatively, any one or more of these components may be packaged separately in housings. The particular configurations for the vibrational transducer has been set forth above, where the vibrational transducer will optionally further be adapted to preferentially deliver the vibrational energy to either the ventricular region of the heart, the atrial region of the heart, or in some instances both, depending on the intended use of the system. In specific embodiments, the control circuitry further comprises a power amplifier, an impedance matching circuit, and a signal generator, optionally for each segment of the vibrational transducer in the case where the transducer aperture comprises multiple individual elements. Usually, for implantable devices, the control circuitry will further comprise a battery or a remotely rechargeable battery and optionally further a transmitter and/or receiver for communication with an external controller. In all implantable systems, the electrical contacts will typically comprise subcutaneously and/or transvenously implantable leads which extend from the housing to the heart or are a part of the housing.

BRIEF DESCRIPTION OF THE DRAWINGS

FIG. 1A shows the pulse repetition period (PRP) while FIG. 1B shows the details of a single burst or pulse.

DETAILED DESCRIPTION OF THE INVENTION

The present invention achieves improved treatment of cardiac arrhythmias by exposing the heart, concurrently or sequentially, to two different energy sources at least comprising vibrational energy and electrical energy. The separate energy sources are selected to stimulate or otherwise affect the same ion channels, different ion channels, or combinations of the same and different ion channels. Such combined stimulation of the ion channels using different energy sources provides enhanced treatment of arrhythmias, particularly allowing the use of lower electrical energy which is less painful and distressing to the patient. It is contemplated, however, that in some instances higher electrical energies typical of those presently employed in defibrillation may also be employed in combination with vibrational energy, where a more reliable termination of an arrhythmia may be achieved. More reliable termination of fibrillation would reduce the need for multiple electrical energy deliveries for a single arrhythmia episode, thus reducing the patient's exposure to painful shocks and conserving battery power.

The present invention relies on directing vibrational energy, particularly ultrasound energy and electrical energy, into cardiac tissue in order to terminate an arrhythmia. An understanding of the nature of ultrasound energy and biological tissue is of use.

Figure 1A:
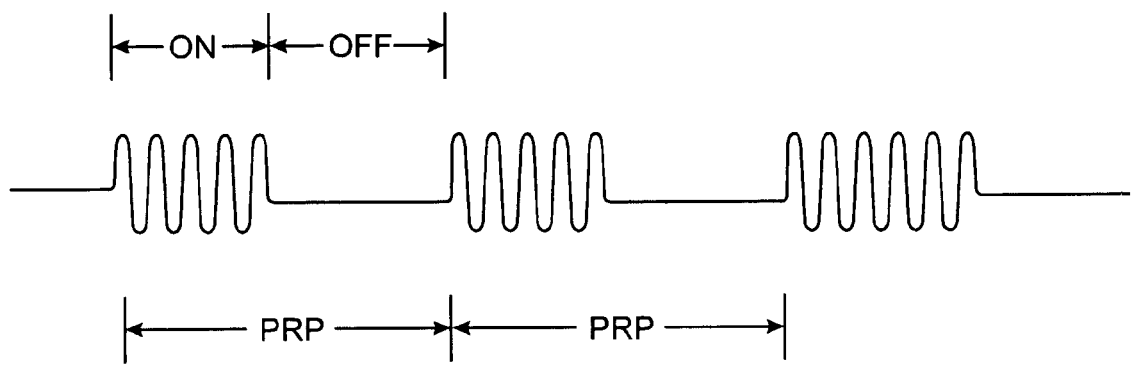
FIGS. 1A and 1B are schematic illustrations of a longitudinal vibrational wave traveling through biological tissue.
Figure 1B:
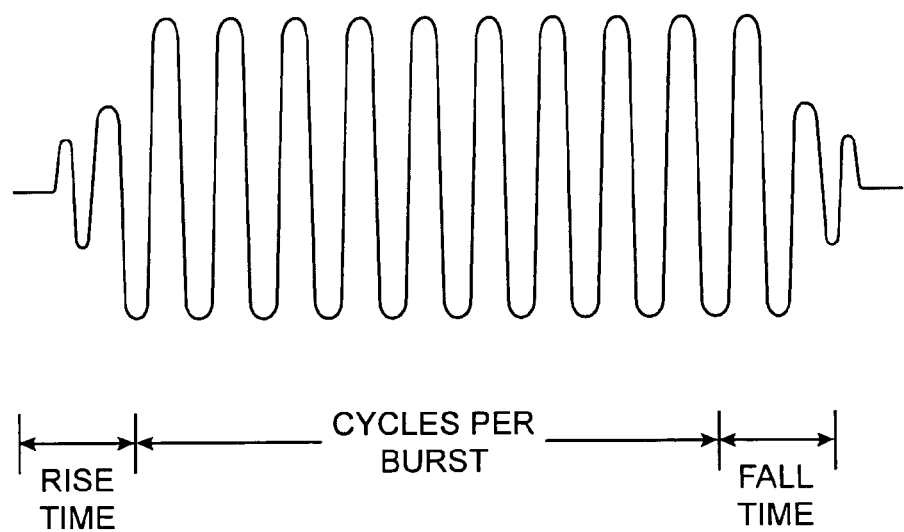

Ultrasound in biological tissues is virtually exclusively a longitudinal traveling wave, as illustrated in FIGS. 1A and 1B. The wave travels at typically 1.5 millimeters per microsecond, in a straight line unless reflected or refracted. Ultrasound may be CW (continuous wave), meaning it is on all the time, or burst mode, comprising periods of ON time separated by lengths of OFF time. The lengths of the ON and OFF periods may be the same or different, and the total of the "on time" and "off time" is referred to as the pulse repetition period (PRP). As illustrated in FIG. 1, ultrasound waves do not come up to peak amplitude instantaneously. The number of cycles involved in the rise time and the fall time are approximately equal to the Q (quality factor) of the device. The period of an ultrasound wave is the time for one complete cycle. The reciprocal of period is the frequency. Bursts may occur at any selected frequency, and the burst rate is defined as the pulse repetition frequency (PRF), which is the reciprocal of the pulse repetition period (1/PRP). The amplitude of the wave can be defined in terms of pressure. In power applications, the magnitude of peak positive pressure is usually greater than that of the peak negative pressure. The waveform is slightly asymmetric due to non-linearities. These non-linearities arise from different velocities of sound in the body as a function of signal strength, and are dependent on the distance of travel through tissue and of course, amplitude.

From the above basic descriptors, other ultrasound parameters follow. The duty cycle is defined as the percent of time the ultrasound is in the ON state. Thus, a continuous wave would have a duty cycle of 100 percent. Intensity is the ultrasound power per unit area. Further common definitions are Ispta (intensity, spatial peak temporal average), the average intensity in the center of the beam over all time, and Isppa (intensity, spatial peak pulse average), the average intensity in the center of the beam averaged only over the duration of the pulse.

Two more parameters are the Mechanical Index (MI) and the Thermal Index (TI). MI is defined as the peak negative pressure in units of MPa divided by the square root of frequency in units of MHz. The parameter is defined for diagnostic ultrasound and reflects the ability of ultrasound to cause mechanical damage, across a wide range of frequencies. The FDA guideline for diagnostic ultrasound allows a maximum MI=1.9. TI for soft tissues is defined as the average power in the beam in milliwatts times the frequency in MHz divided by 210. TI defines the capability of ultrasound to create thermal bioeffects in tissue, and a value of unity corresponds to a theoretical temperature rise in normal tissue of one Centigrade degree. These expressions show important trends for ultrasound. For a given pressure, lower frequencies tend to result in greater mechanical bioeffects. Further, for higher frequencies, there is a stronger tendency for greater thermal bioeffects.

An ultrasound beam is attenuated by the tissues through which it propagates. Tissue motion has no effect on ultrasound attenuation. At frequencies below 5 MHz, attenuation in blood is negligible. Attenuation in myocardium, muscle, fat, and skin is approximately 0.3 dB per MHz per centimeter of propagation path. Consequently, a 1 MHz beam will suffer little attenuation through the body wall and heart. All frequencies of ultrasound do not propagate well through air; it is virtually totally attenuated. The lungs and bowel gas essentially totally obstruct the beam. Attenuation in bone is strongly frequency-dependent. The attenuation at 1 MHz is in excess of 12 dB per centimeter, rising almost linearly with frequency. At 100 kHz, attenuation is negligible.

Figure 3:
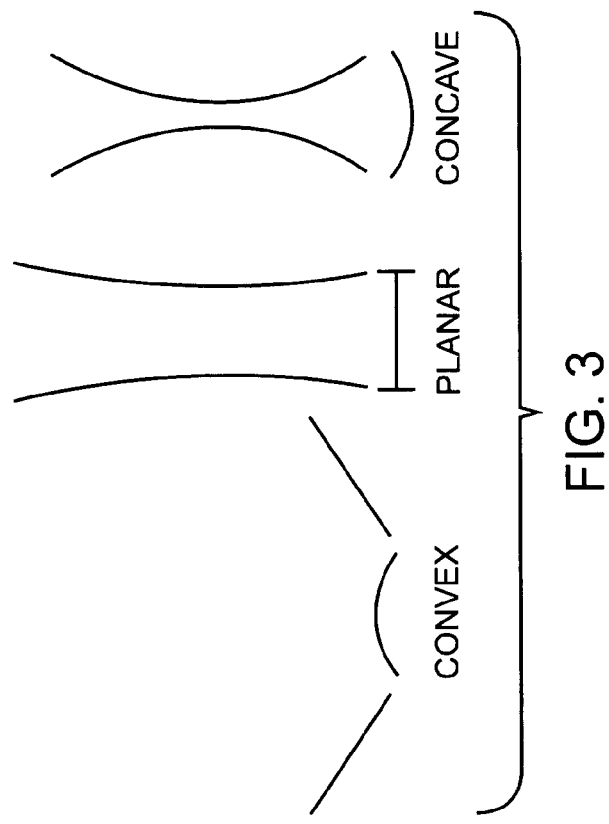
FIG. 3 illustrates high frequency beams from convex, flat, and concave apertures which form divergent, mildly focused, and sharply focused beams, respectively.
Figure 2:
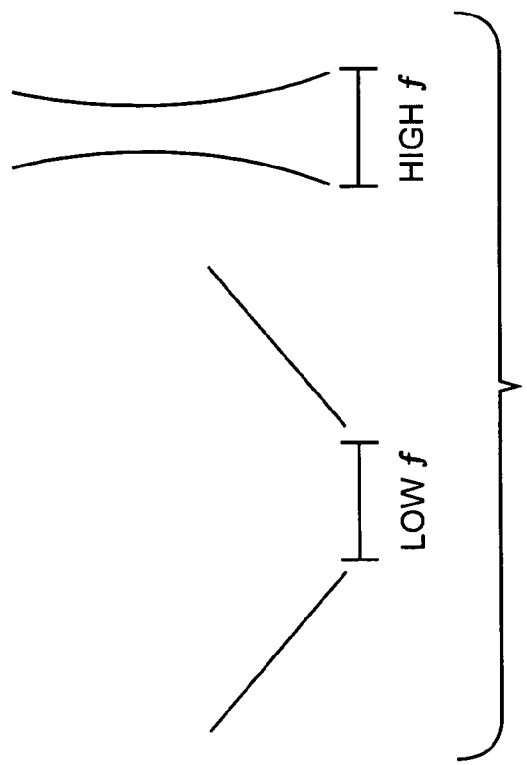
FIG. 2 is a schematic illustration of the relationship between frequency (wavelength) and focus of an ultrasonic beam.

Ultrasonic beams are highly dependent on the aperture of the radiator and the frequency, and whether the beam is continuous wave burst mode. A simple rule is that in the far field, the beam width is given by the wavelength divided by the aperture. Given the same sized apertures, a low frequency (Low f) beam might be almost isotropic (equal intensity in all directions) while a high frequency (High f) beam will be focused, as illustrated in FIG. 2. Further, the shape of the aperture will affect the beam. FIG. 3 depicts high frequency beams from convex, planar, and concave apertures, forming divergent, mildly focused, and sharply focused beams, respectively. In the far field, pulsed and continuous beams have approximately the same profiles. In the near field, however, continuous beams are characterized by multiple peaks and valleys due to constructive and destructive interference, respectively, of wavefronts from across the aperture. (In the near field for short bursts of ultrasound, constructive and destructive interference is limited to emissions from smaller portions of the aperture, and consequently, near field emission profiles are more uniform.)

Figure 4B:
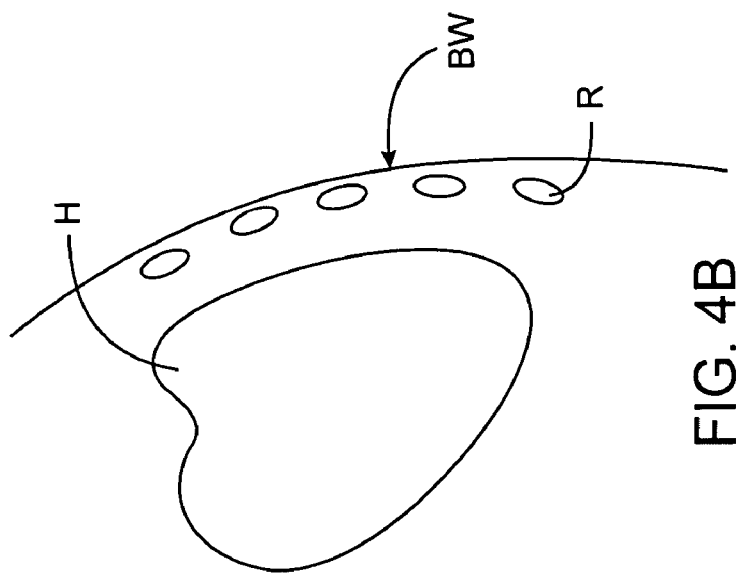
FIGS. 4A and 4B illustrate the anatomy in which the vibrational transducers of the present invention are to be implanted.
Figure 4A:
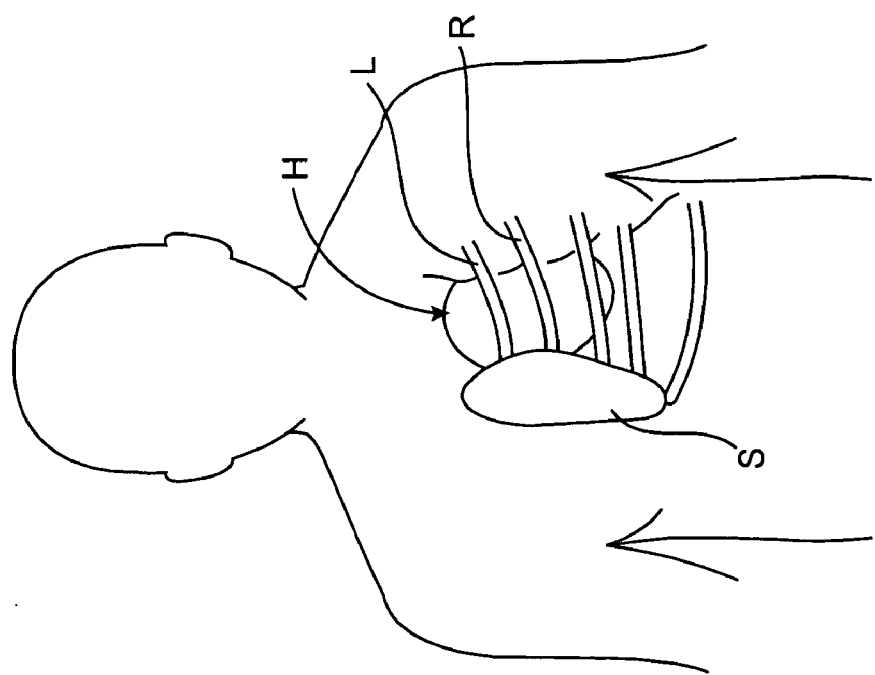

Referring now to FIGS. 4A and 4B, the present invention relies in part on directing ultrasound and other vibrational energy to the heart H in order to stabilize cardiac electrical activity as generally discussed above. In particular, for defibrillation, it is desirable to be able to direct the ultrasonic energy over as great a portion of the heart volume, e.g., the aspect closest to the chest, as possible in order to assure maximum effectiveness. Usually, for defibrillation, the present invention will provide for directing the ultrasonic energy to at least 50% of the cardiac tissue, preferably at least 75%, and more preferably 90% or greater. Usually, for pacing treatment, the vibrational energy will be delivered to less than 50% of the heart. As the heart is located beneath the body wall (BW), ribs R and sternum S, however, the vibrational transducer assembly (as described in greater detail below) must be properly located to deliver the energy. Bone and cartilage significantly attenuate the propagation of high frequency ultrasonic energy, and the lungs L (which are filled with air) will totally obstruct the transmission of such energy.

Figure 5C:
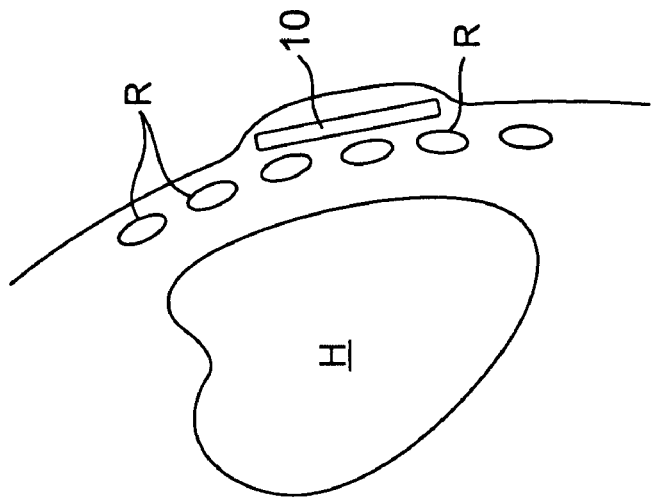
FIGS. 5A–5C illustrate alternative implantation sites for the vibrational transducers and transducer assemblies of the present invention.
Figure 5B:
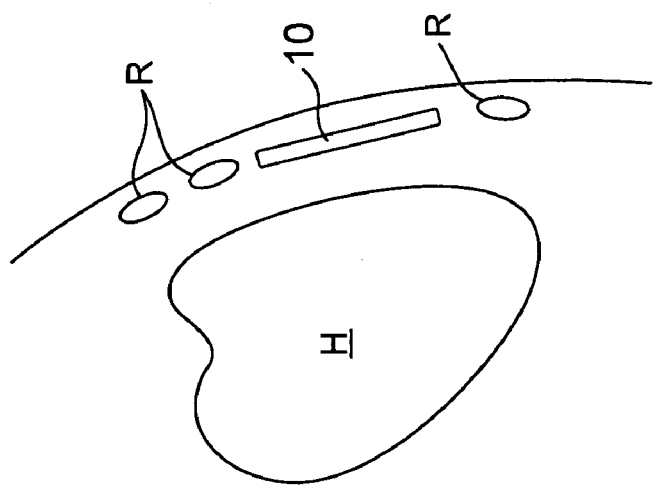
Figure 5A:
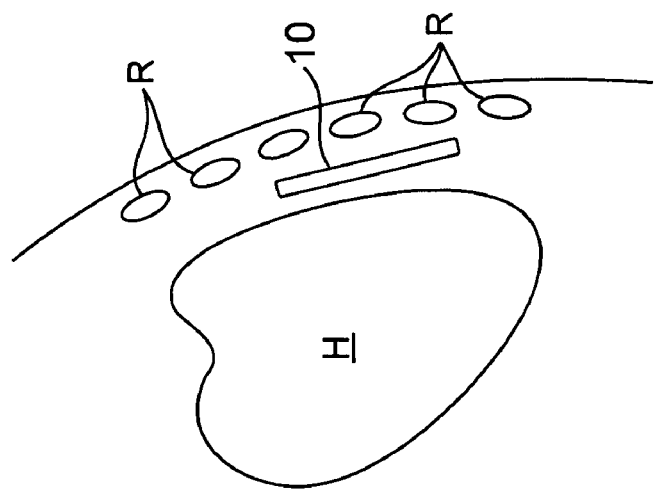

For the treatment of ventricular arrhythmias, it will generally be preferred to implant a vibrational transducer assembly 10 either over the ribs R, as shown in FIG. 5C, between or in place of the ribs R and/or sternum, as shown in FIG. 5B, or perhaps less desirably under the ribs R, as shown in FIG. 5A. When implanted beneath the ribs, the vibrational transducer assembly 10 will usually be placed over or spaced slightly anteriorly from the pericardium. Alternatively, but not shown, the transducer assembly may be implanted in the abdomen, either within or outside of the peritoneal cavity.

For the treatment of atrial arrhythmias, the vibrational transducer is preferably disposed to preferentially deliver the vibrational energy to the atrial regions of the heart. Because of the different anatomical location of the atrium, it will be possible to place the vibrational transducer(s) either or both anteriorly or posteriorly on the patient. The anterior implantable locations may generally be the same as described above with respect to FIGS. 5A–C, except that the precise position may be changed to overlie the atrium instead of the ventricle. Alternatively or additionally, the direction at which the vibrational energy is directed from the implanted device may also be modified to preferentially target the atrium as opposed to the ventricle. Particular posterior implantable locations are described in pending U.S. patent application Ser. No. 10/869,776 filed on the same date as the present application, the full disclosure of which has previously been incorporated herein by reference.

Figure 6:
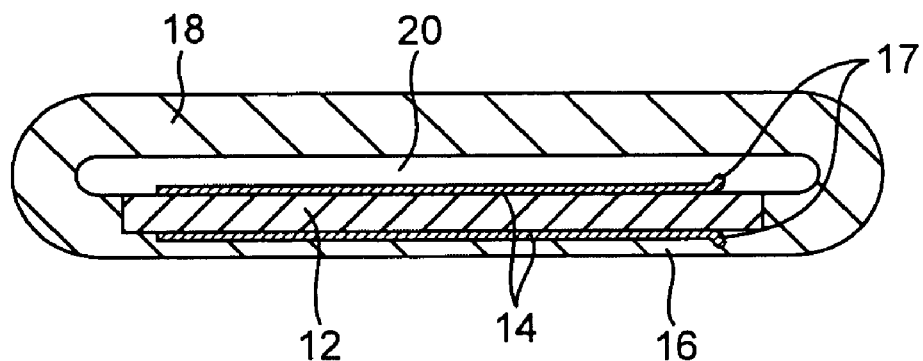
FIG. 6 illustrates a first embodiment of a vibrational transducer assembly constructed in accordance with the principles of the present invention.

Referring now to FIG. 6, a first exemplary vibrational transducer assembly 10A comprises a quarter wave front surface matched device. A half-wave thickness of piezo electric ceramic 12 is sandwiched between thin layer electrodes 14 having leads 17 and with a quarter-wave matching layer 16 disposed over the first surface. The piezo electric ceramic 12 is positioned in a housing 18 with an air cavity 20 at its rear surface. In this way, the quarter-wave matching layer 16 provides a front surface of the assembly 10A, and the edges and back of the housing need only be strong enough to provide mechanical support. The air cavity 20 will typically have a width of about 1 mm, and the thickness of the ceramic and matching layer will vary depending on the desired frequency of operation. Table 1 below shows the operational frequencies and thicknesses of the ceramic layer 12 and matching layer 16.

TABLE 1

| Device Frequency (MHz) | Ceramic Thickness (mm) | Matching Thickness (mm) |
|---|---|---|
| 2.0 | 1.0 | 0.37 |
| 1.0 | 2.0 | 0.75 |
| 0.5 | 4.0 | 1.5 |
| 0.25 | 8.0 | 3.0 |
| 0.10 | 20.0 | 7.5 |

The methods of the present invention likely result from the mechanical effects of ultrasound. As such, the maximum frequency might be on the order of 1 MHz. From a structural point of view, at 0.10 MHz, the device package thickness might be on the order of 30 mm thick, probably the maximum acceptable for an implant. If the device needs to be implanted over the ribs and/or sternum or placed externally, the lower frequencies are preferred. At 0.25 MHz, the attenuation due to bone might be minimal, thus suggesting an operational frequency in the 0.10 to 0.5 MHz range.

Operating below 0.25 MHz with a conventional quarter wave device may not be especially advantageous due to the higher voltages needed to drive the device. Also, as the device gets thicker, it becomes substantially heavier.

Not shown, the transducer assembly 10A may be substituted with a 1–3 piezo-composite material instead of the ceramic. Piezo-composite material consists of piezoelectric ceramic posts in a polymer matrix. Such materials are thinner than the equivalent pure ceramic material needed to achieve a particular frequency and there is no need to provide a matching layer. Thus, a simple high-voltage seal may be substituted for the matching layer 16 of FIG. 6. Suitable thicknesses for the piezo-composite material are shown in Table 2 below.

TABLE 2

| Device Frequency (MHz) | Piezo-composite Thickness (mm) |
|---|---|
| 2.0 | 0.75 |
| 1.0 | 1.5 |
| 0.5 | 3.0 |
| 0.25 | 6.0 |
| 0.10 | 15.0 |

Besides creating a thinner package, the piezo-composite materials have another significant benefit in that they can be easily curved, potentially to conform to anatomical features or optimize the transducer beam profile. It must be remembered that any curvature will affect the focal characteristics of the device.

Figure 7:
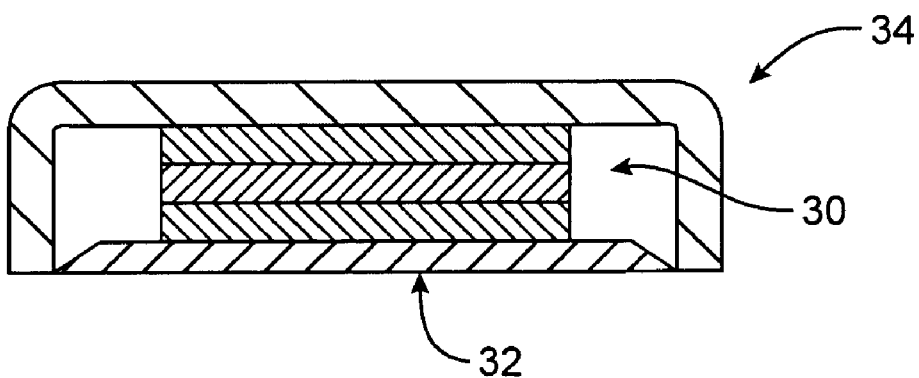
FIG. 7 illustrates a second embodiment of a vibrational transducer assembly constructed in accordance with the principles of the present invention.

Referring now to FIG. 7, a vibrational transducer assembly 10B may be formed as a variation on a Tonpilz transducer where a piezo drive 30 (shown as a stack of piezoelectric material) induces ultrasonic vibration on a front vibrator 32. The package 34 provides the necessary tail mass for operation of the transducer assembly. Optionally, a structure (not shown) for retaining the front surface vibrator 32 against the ceramic stack 30 and housing 34 may be provided. Strong vibrations of the surface vibrator may exceed the tensile strength of the ceramic and/or bonding material. Such transducer assemblies are particularly well suited to operation at low frequencies, 0.1 MHz and below.

For defibrillation, the device of the present invention will require an aperture generating a relatively wide acoustic beam in order to deliver ultrasonic or other vibrational energy over a relatively large portion of the heart. Due to biological constraints, the transducer may be in proximity to the heart, and as such, the heart may be in the near field of the acoustic beam. With typical human heart dimensions of 12 cm in length and 10 cm in width, the ultrasonic or other vibrational energy aperture will typically be circular with a diameter on the order of 10 cm, more preferably elliptical with long and short axes of 12 and 10 cm, and most preferably elliptical with the ultrasonic or other vibrational energy aperture slightly exceeding the dimensions of the heart to assure maximal coverage of myocardium with therapeutic energy. It is recognized that many different sizes of devices might be required to meet the needs of different patient sizes.

Figure 8:
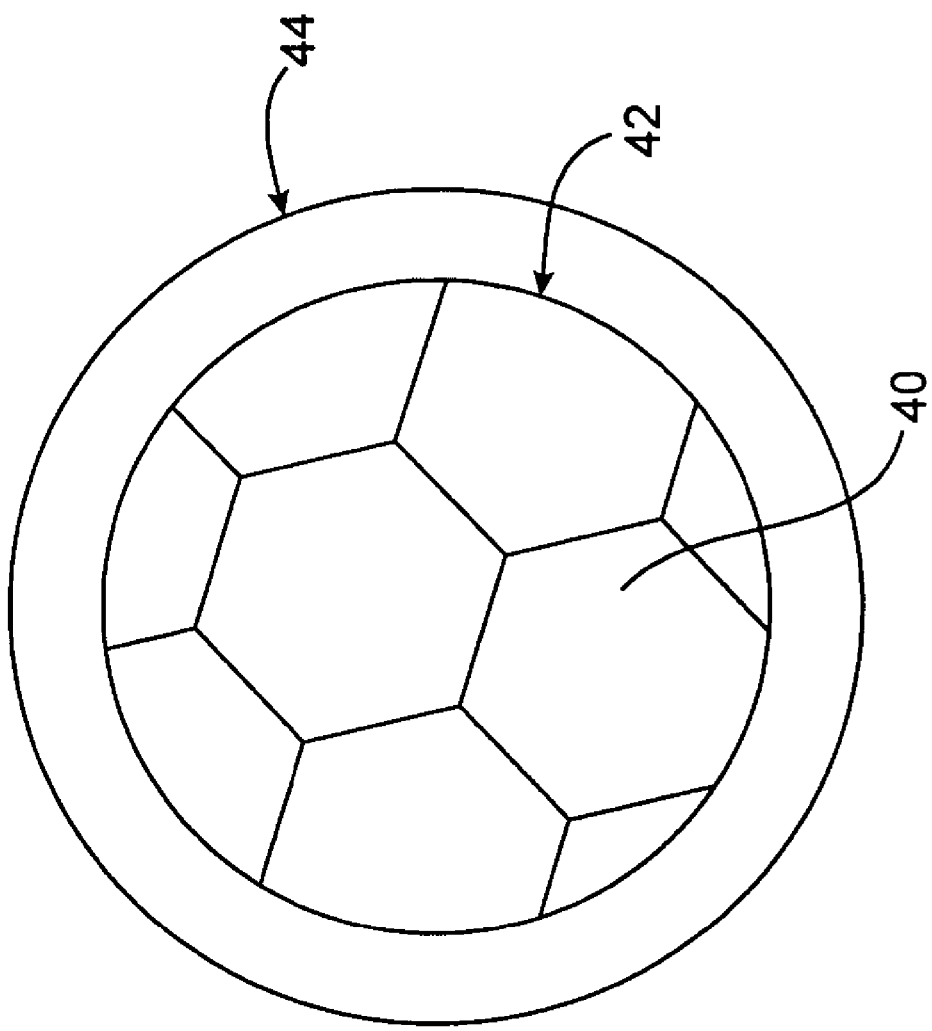
FIG. 8 illustrates a third embodiment of a vibrational transducer assembly constructed in accordance with the principles of the present invention.

Further variations on device design are possible. Specifically, recently developed high strain materials such as single crystal or polymer piezo-electrics might be employed. In the case of the single crystals, current technology does not provide material with dimensions consistent with the sizes projected to cover a significant fraction of the heart. Consequently, a mosaic structure of individual pieces or sections 40 of piezo electric material, as depicted in FIG. 8, might be employed. The sections 40 are arranged within an ultrasonic radiative aperture 42 in a casing 44. The sizes of individual pieces would be consistent with current manufacturing technology, currently approximately one inch on the side. The single crystals may have individual signal generators, driving amplifiers, and/or impedance matching circuits for parallel or serial operation. Alternatively, the single crystals may be driven in a sequential (multiplexed) manner by a single signal generator, power amplifier, and matching layer. The single crystals may employ front surface impedance matching (quarter wave thicknesses) as used for the conventional piezo-electrics as depicted in FIG. 6. The mosaic of individual pieces may be mounted on a flat coplanar surface, or the devices might be so mounted as to give the front surface of the device either a concave or convex surface for better implantation under the patient's skin. Likewise, the polymer devices might be flat or curved, as appropriate for acoustic coupling beneath the patient's skin. Polymer devices probably will not require a front surface impedance matching layer, but may be backed with a high impedance backing layer to project as much of the acoustic energy out into the patient as possible. Driving materials for transducers may also include any other electro-mechanical material, one specific example being magnetostrictive materials.

The device may be driven with a high voltage and a high current. After appropriate electrical impedance matching, the current drain on the battery may exceed the capability of the same. It is thus proposed to segment the aperture into multiple individual pieces of piezoelectric, as depicted in FIG. 8 and as described above. In this case, each element may be driven by an individual power amplifier, impedance matching circuit, and signal generator (or a signal generator gated to individual devices). Alternatively, the single crystals may be driven in a sequential (multiplexed) manner by a single signal generator, power amplifier, and matching layer. As such then, exposure of the heart would be segmental. If, for example, the aperture consisted of 10 elements, operating with 5 cycles at 1 MHz, each element might be triggered every 50 microseconds, allowing for an effective 10 percent duty cycle. This would reduce the current demand on the battery by a factor of 10.

Figure 9B:
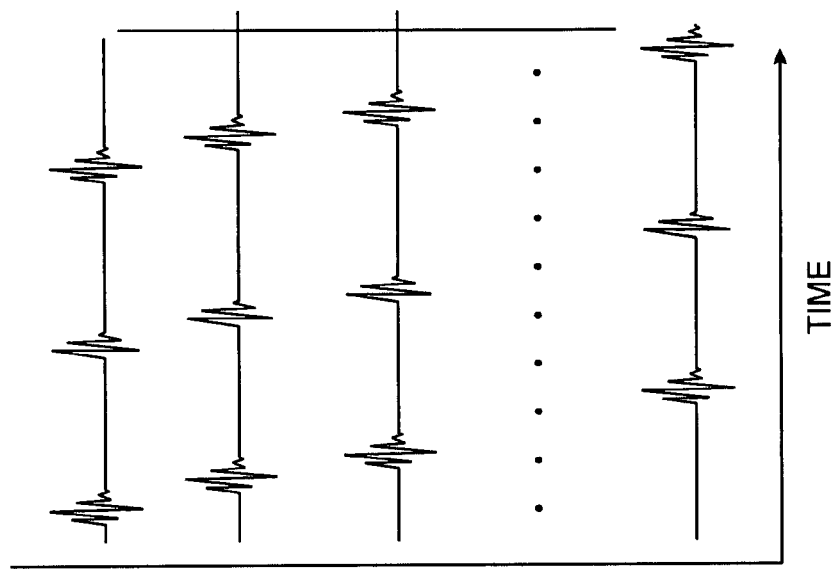
FIGS. 9A and 9B illustrate a circuit configuration (FIG. 9A) and serial burst pattern (FIG. 9B) which would be suitable for operating the vibrational transducer assembly of FIG. 8.
Figure 9A:
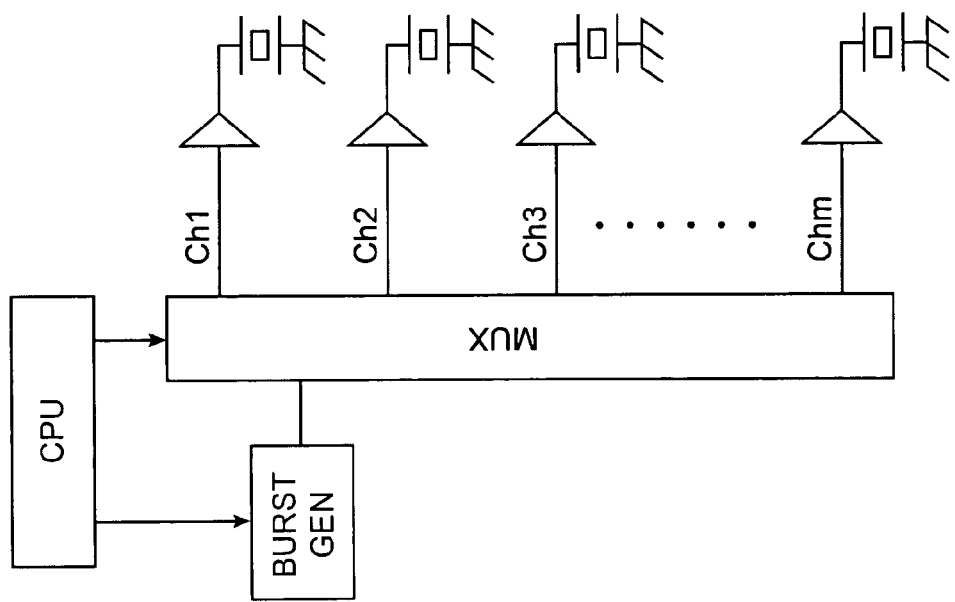

FIGS. 9A and 9B depict one possible circuit configuration for generating serial bursts from the segmented aperture, and further depicts the interlaced output from each of the individual elements within the aperture. It is possible to generate multiple bursts from every element during a small fraction of the cardiac cycle. The myocardium will effectively experience simultaneous ultrasound exposure. Care must be exercised in the implementation of this concept to prevent excessive beam spreading from the smaller elements and loss of far field signal strength. Low frequency devices would be more prone to this problem than high frequency devices.

Alternatively, the segmented aperture of individual elements of electro mechanical material, or clusters of one to several posts of a piezo composite material, may be driven in a phased sequence, so as to create an ultrasound beam in one of several particular directions. "Phasing" means that the driving signals applied to all elements or segments of the aperture have time delays such that the wavefronts from each element or segment arrive at a designated tissue mass at the same time (constructive interference). Although the amplitude in this tissue mass will be greater due to the focusing effect of the phased aperture, the beam may no longer cover the entire region of tissue requiring treatment. Consequently, in rapid succession, on time scales very small compared to the time of the cardiac cycle, the beam may be directed to multiple tissue masses in the region of treatment, so as to effectively uniformly expose the entire region with ultrasound.

Circuit configurations for operation in a phased array mode may be quite similar to the circuit configuration depicted in FIG. 9A. For phased array operation, all elements would be operative at the same time, albeit with different time delays. The burst generator would provide the different time delays which would be directed to specific amplifiers/elements through the multiplexer (MUX). Multiple sets of time delays would result in beams in multiple directions.

Instead of segmenting the aperture in a compact two-dimensional format, the aperture may be comprised of a series of segments or elements in a linear arrangement. Such an array of elements may be implanted or fixed externally for directing vibrational energy to the heart from between the ribs. Indeed, a second string of elements could be implemented in similar format, for directing vibrational energy to the heart through another intercostal space, either above or below the first string of elements. Alternatively or in conjunction, a string of elements may be implemented over the sternum. Although there will be some attenuation of the ultrasonic beam, directing vibrational energy through the sternum will assure a pathway to the heart unimpeded by lung tissue. The single or multiple linear strands of aperture segments or elements can be electrically driven in parallel or in serial format, or driven in a phased format for targeting of a specific region of the heart, or for sweeping the ultrasonic beam across a greater portion of the heart.

For pacing therapy, the device of the present invention may not require an aperture for generating a wide acoustic beam since it is not necessary for the acoustic beam to deliver energy to the majority of the heart. Thus, pacing may be accomplished by delivering vibrational energy from a portion of the transducer aperture using a segmental design, or alternatively, from a separate transducer aperture generating a narrower acoustic beam. If using a separate transducer, the separate transducer may be smaller in size and of a different shape. Thus, the invention may be comprised of one or more that one transducer assembly, connected by a cable (not illustrated).

It is assumed that the desired effect is a mechanical effect. Operating a transducer in continuous wave mode creates a maximum thermal effect and a minimal mechanical effect. Operating in burst mode with a low duty cycle and a high amplitude minimizes thermal effects and maximizes mechanical effects. It is further believed, with some empirical evidence, that high burst rates (and short burst lengths) provide the yet further enhancements to a mechanical effect. Consequently, a preferred design will be for shortest possible burst lengths, maximum amplitude, and duty cycle to the thermal limit.

The above paragraphs discussed some of the packaging considerations for the transducer portion of the device. To summarize, the overhead on the aperture is expected to be minimal, perhaps adding 5 to 10 mm to the diameter of a device. The thickness of the device will be defined by the type and the frequency. The electronics package (and battery) can be combined with the transducer or can be separately housed, with a cable between the two units.

Figure 10:
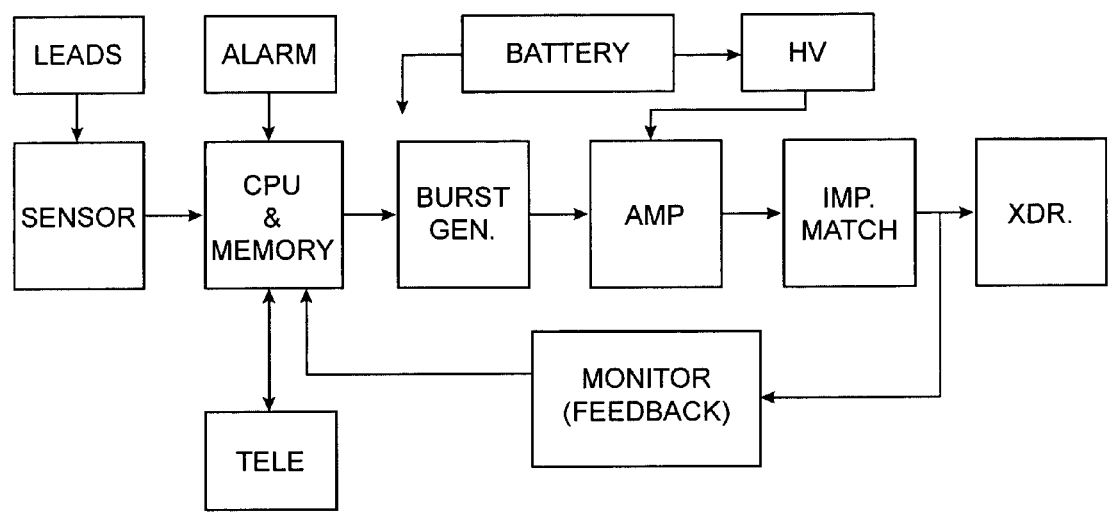
FIG. 10 is a block diagram showing an embodiment of the control circuitry implementation of the present invention.

FIG. 10 represents a block diagram of a possible electronics package for the vibrational portion of the device. The sensor circuit would be monitoring the heart and the power side of the system would generally remain idle until such time an arrhythmia event were to occur. The sensor circuits may be integral with the CPU. Once an event is detected, the CPU would trigger the burst generator which would generate a preprogrammed series of bursts, until such time as the heart has returned to normal rhythm. The electrical bursts would pass to a power amplifier, an impedance matching circuit, and on to the transducer. A battery would supply power for the typically digital circuits in the CPU, telemetry, sensor, and burst generator, the typically analog circuits in the front ends of the sensor and amplifier, and to a voltage converter which produces the high voltage for the output stages of the amplifier. Monitoring circuitry would provide feedback to the CPU about the actual performance of the power amplifier and transducer(s).

The operational life of a defibrillator system may be expected to be on the order of that for an implantable ICD. The operational life of a pacing system may be on the order of a year or more progressing up to 5 years. A battery volume similar to that used in an ICD is anticipated. The amplifier and impedance matching circuits might require on the order of 25 cubic centimeters of volume, and the digital portions on the order of 5 cubic centimeters. In all, it is reasonable to assume that the package could be implanted into the chest of a human. Use of a rechargeable battery system utilizing transcutaneous inductive energy transmission may be beneficial.

The circuitry of FIG. 10 may be adapted to drive the associated vibrational transducer under conditions which will impart vibrational energy to the heart so that the arrhythmia is terminated. In particular, the vibrational transducer may be operated under the conditions specified in Table 3. The device of the present invention may or may not allow for synchronization of the therapeutic ultrasound or vibrational energy burst to the cardiac cycle. In a first embodiment, once a rhythm abnormality is detected, the system will immediately initiate the preprogrammed therapeutic protocol, irrespective of the time point on the cardiac cycle. In a second embodiment, the system may trigger during any time within prespecified intervals of the cardiac cycle. In yet a third possible embodiment, the system may initially be energized for a preprogrammed protocol, but then fall into a specified time interval of the cardiac cycle as normal rhythm is detected or anticipated.

The duration that the vibrational energy is delivered is a function of the transducer frequency, burst length (number of cycles), burst rate, and duty cycle. It is anticipated that the vibrational therapy might be applied for a duration less than one complete cardiac cycle. It is further anticipated that the vibrational energy therapy might be repeated for more than one cardiac cycle.

TABLE 3

| Parameter | Cardioversion and Defibrillation | | | Pacing |
| --- | --- | --- | --- | --- |
| | Preferred Implementation | More preferred Implementation | Most preferred Implementation | Most preferred Implementation |
| Frequency (MHz) | 0.020–10.0 | 0.050–1.00 | 0.100–0.300 | 0.25–0.50 |
| Burst length (cycles) | <5000 | <500 | <50 | <50 |
| Burst rate (Hz) | >10 | ≧100 | ≧100 | Single burst |
| Duty cycle (%) | <50 | <10 | <5 | 100 |
| No. of cardiac cycles | as required | <5 | 1 | All |
| Duration (msec) | <200 | <50 | <20 | <0.2 |
| MI | <50 | <25 | <15 | <2 |
| TI | <4 | <1 | <.1 | <0.10 |
| Myocardial Coverage (%) | >50 | >75 | >90 | <20 |
| Cardiac cycles from sense to trigger | <10 | <5 | <2 | 0 or 1 |

The apparatus of the present invention will also require electrical contacts and circuitry for delivering electrical energy to the heart for cardioversion or defibrillation. The circuitry, electrical contacts, and other aspects of the system may generally be similar to the implantable and external defibrillators which are presently available and well described in the medical and patent literature. For example, suitable external defibrillator circuitry and systems may be combined with the vibrational systems of the present invention and are described in U.S. Pat. Nos. 6,567,698; 6,047,212; 5,891,173; 5,879,374; 5,643,324; 5,607,454; 5,593,428; 5,411,537; 4,825,871; and 4,198,963.

Similarly, power supplies and circuitries suitable for delivering electrical energy using the implantable apparatus of the present invention are described in U.S. Pat. Nos. 6,327,499; 6,292,691; 6,282,444; 6,184,160; 6,085,116; 6,081,746; 6,076,014; 6,006,131; 5,904,705; 5,899,923; 5,861,006; 5,755,742; 5,720,767; 5,540,721; 5,514,160; 5,447,522; 5,439,482; 5,431,685; 5,413,592; 5,411,537; and 5,407,444.

The full disclosures of each of these listed prior U.S. Patents listed in the paragraphs above are incorporated herein by reference.

The systems of the present invention may be adapted for total or partial implantation or, alternatively, may be intended for external use only. The external systems may be configured in a manner similar to that for conventional electrical external defibrillators, typically including a control unit, external paddles or other electrical contacts for placing on spaced-apart locations on the patient's chest, and further including a component for externally applying vibrational energy in either or both anterior or posterior locations on the patient's chest.

Figure 11:
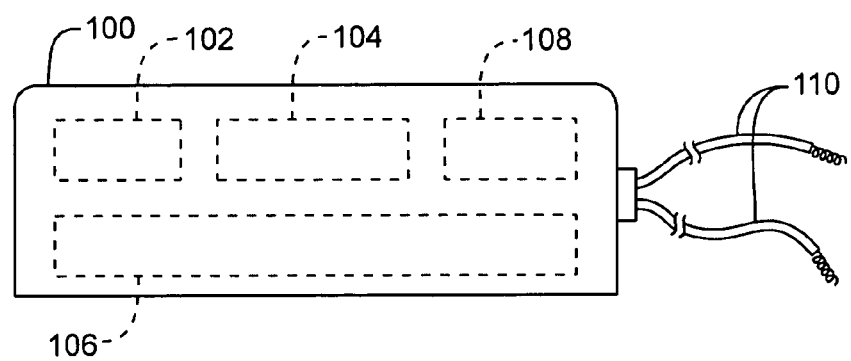
FIG. 11 illustrates a system for stabilizing cardiac arrhythmias constructed in accordance with the principles of the present invention, where all system components are incorporated in a single housing.
Figure 12:
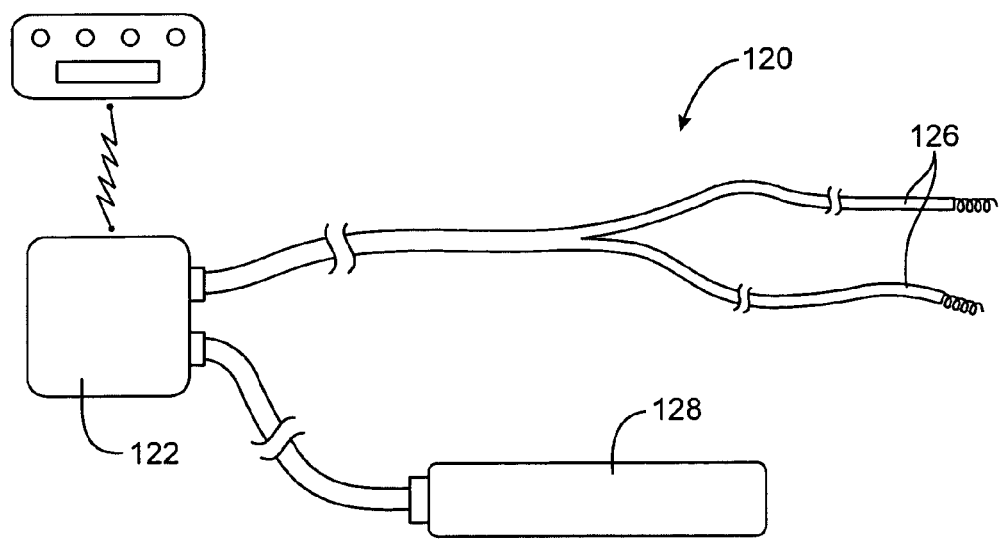
FIG. 12 illustrates an alternative embodiment of a system for stabilizing cardiac arrhythmias according to the present invention, where the control circuitry, the electrical contacts, and the vibrational transducer are all provided in separate, implantable modules.

Referring to FIGS. 11 and 12, alternative systems of the present invention which are implantable may include components disposed entirely within a common housing, as shown in FIG. 11, or components contained within a plurality of separate housings or modules (FIG. 12). A common housing 100 may include all internal power and control circuitry necessary for operating the system. For example, circuitry 102 may be provided for powering the unit, typically including a battery, circuitry 104 may be provided for controlling vibrational transducer 106, and circuitry 108 may be provided for controlling and powering electrode leads 110. Electrode leads 110, in turn, may be configured either for subcutaneous or intravenous implantation, or alternatively and not shown, the electrodes may be placed on the housing.

The cardiac stabilization system 120 illustrated in FIG. 12 includes separately implantable components with housing 122 containing CPU control and power circuitry for both electrical energy and vibrational energy, implantable leads 126, and a vibrational transducer housing 128. Each of these components may be separately implanted at different locations to optimize therapies according to the present invention.

Figure 13:
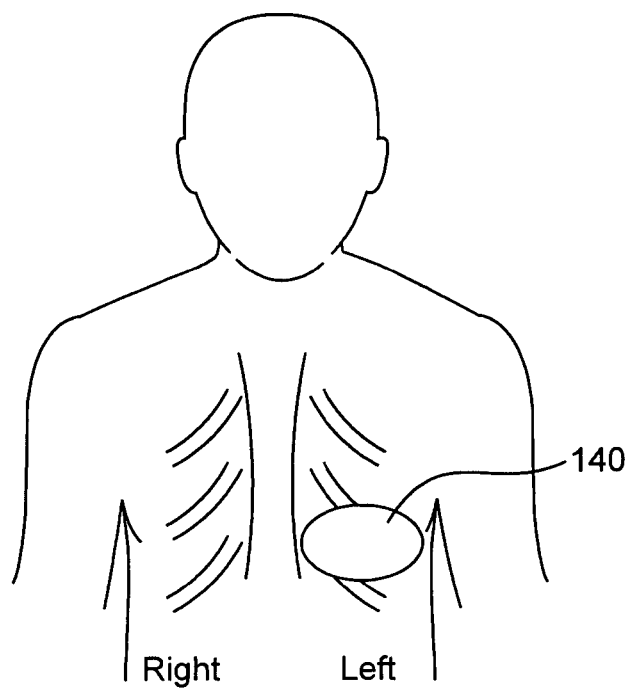
FIG. 13 illustrates implantation of a device according to the present invention, where the device comprises a single housing which passes electrical energy through the body to the heart from electrodes on the housing to provide delivery of the electrical energy.

Referring now to FIG. 13, a system 140 according to the present invention wherein all components are included in a single housing as shown implanted anteriorly over the lower rib cage. The system 140 includes electrical contacts built into the housing and will typically be implanted so that these integrated contacts may directly activate the ventricular or atrial aspect of the heart.

Figure 14A:
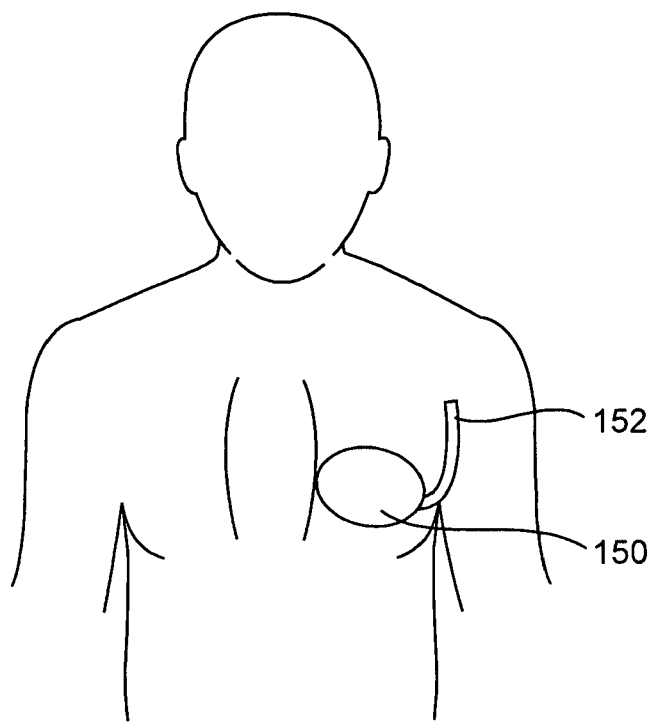
FIGS. 14A and 14B illustrate the implantation of an alternative device according to the present invention, where the device includes a single subcutaneous lead which is implanted into the body and which passes electrical energy through the body to the heart from electrodes on the lead.
Figure 14B:
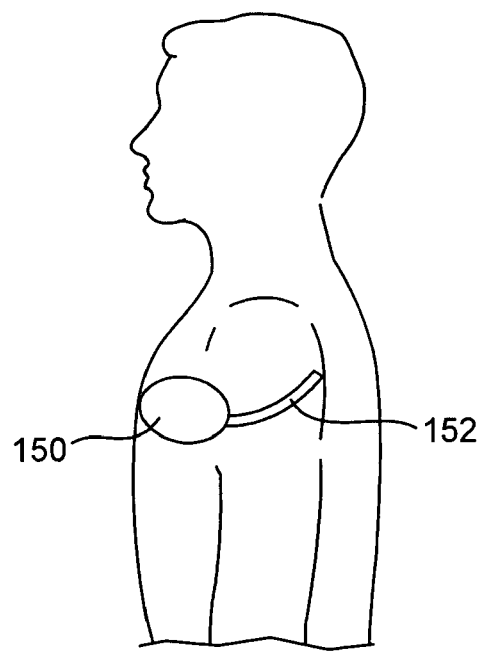

Systems 150 according to the present invention may include a single subcutaneous lead 152 containing both or either electrical or vibrational elements, as shown FIGS. 14A (front view) and 14B (side view). Main housing of the system 150 will include the vibrational transducer and electrical energy components and be implanted in the anterior chest overlying the ventricular or atrial region of the heart. The single subcutaneous lead 152 may then be implanted subcutaneously parallel to the left anterior ribs as illustrated.

Figure 15A:
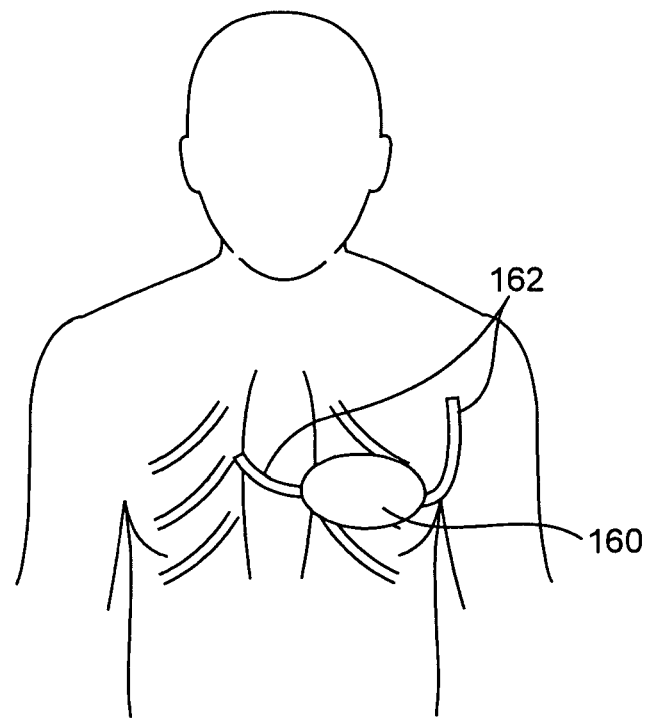
FIGS. 15A and 15B illustrate implantation of a device according to the present invention, where the device includes a pair of subcutaneous leads.
Figure 15B:
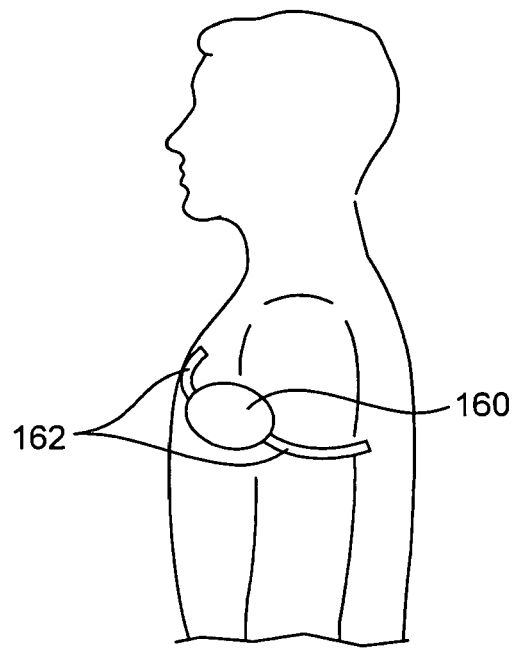

A defibrillation system 160 including a pair of implantable subcutaneous leads 162 as illustrated in FIGS. 15A (front view) and 15B (side view). As with system 150, the housing of system 160 will include the vibrational transducer and electrical energy components and may be implanted to deliver the vibrational energy to the target region of the heart. As illustrated, the housing is implanted in an anterior region of the chest overlying the heart. The subcutaneous leads 162 containing both or either electrical or vibrational elements are then positioned to be implanted subcutaneously over the sternum to the right and parallel to the left anterior ribs as illustrated.

Figure 16:
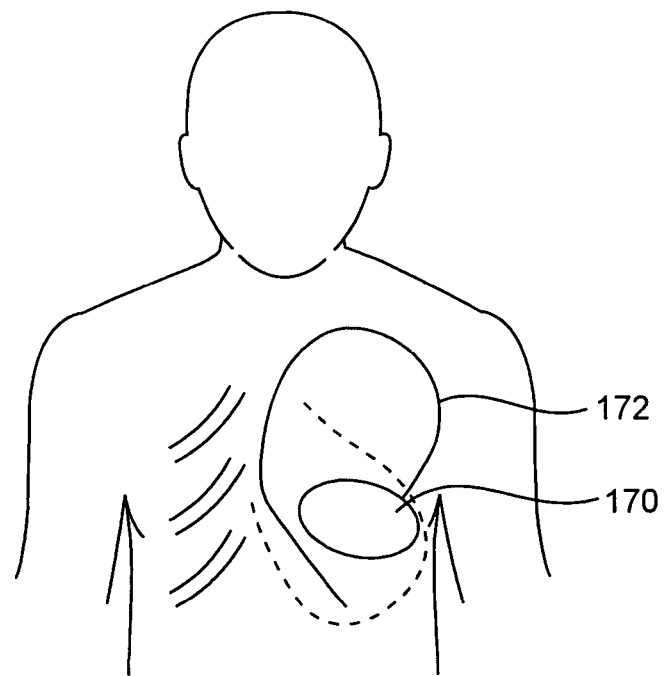
FIG. 16 illustrates implantation of a device according to the present invention, where the device includes a single (multielectrode) transvenous lead implanted into the heart.

Referring now to FIG. 16, a system 170 according to the present invention comprises a transvenously implanted lead 172 which may be implanted directly within an atrium or ventricle of the heart, in a manner conventional for implantable pacemakers and/or defibrillators. The housing 170 includes the vibrational transducer which may be implanted in either or both an anterior or posterior region of the chest in order to deliver vibrational energy to the target ventricular or atrial region of the heart.

Figure 17:
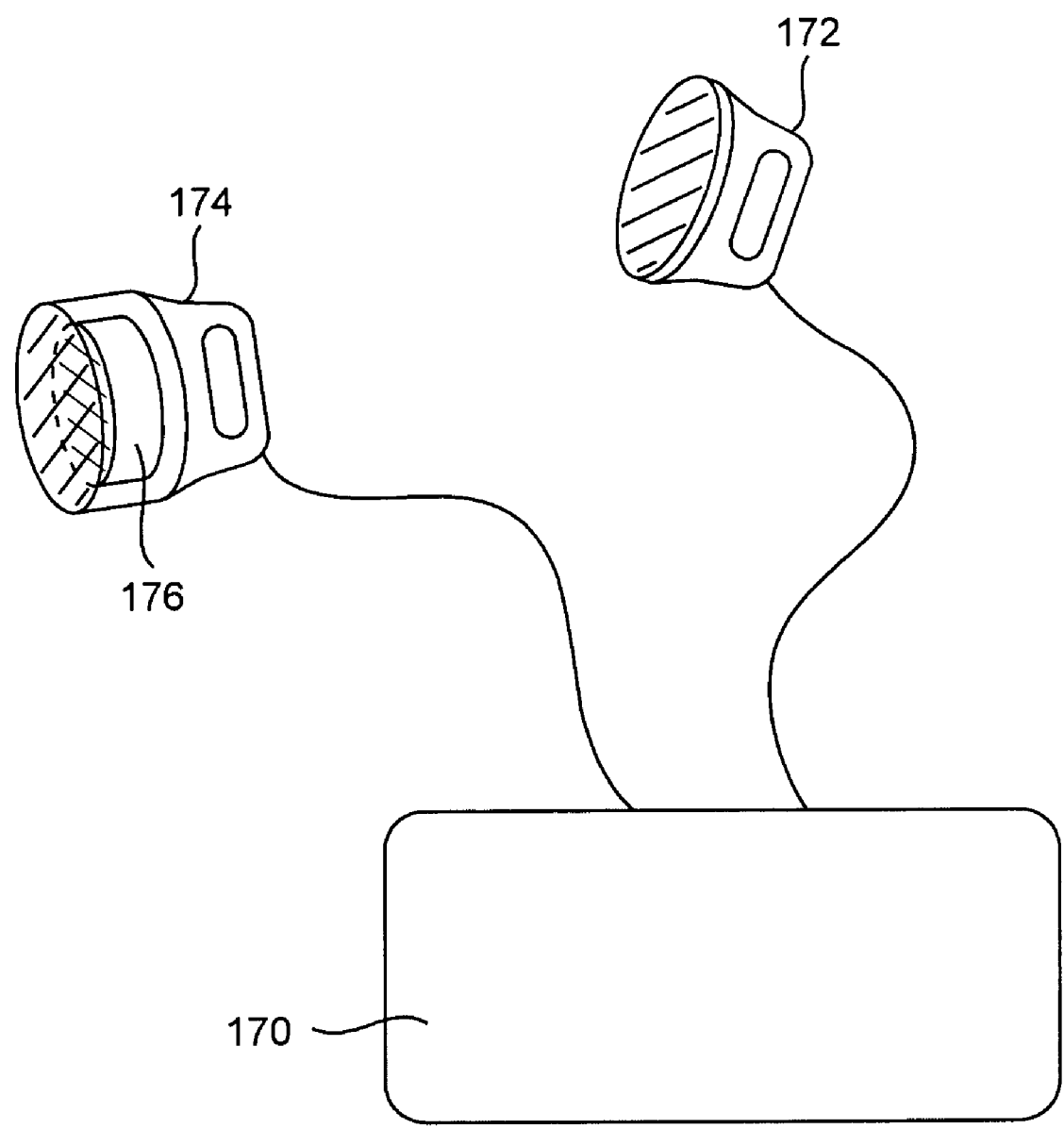
FIG. 17 illustrates the combination of a vibrational energy transducer and electrical energy delivery paddles for external energy delivery.

In the case of externally delivered vibrational energy, the transducer assembly may be a separate component or may be located in either or both of the two electrical energy paddles, as depicted in FIG. 17. The housing 170 controls both the electrical energy paddles 172 and 174 and in this example the vibrational energy transducer 176 within paddle 174. The addition of coupling gel is necessary to delivery for both electrical and vibrational energies from paddles 172 and 174 to the patient.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for stabilizing cardiac arrhythmias, said method comprising:
   delivering controlled vibrational energy from a vibrational transducer to the heart; and
   delivering electrical energy to the heart, wherein the vibrational energy and electrical energy are delivered at least partly simultaneously under conditions which terminate the arrhythmia and the vibrational transducer is not in contact with the heart.

2. A method as in claim 1, wherein delivering at least one of the controlled vibrational energy and the electrical energy is performed by an implanted device.

3. A method as in claim 2, wherein both the controlled vibrational energy and the electrical energy are delivered by an implanted device.

4. A method as in claim 1, wherein delivering at least one of the controlled vibrational energy and the electrical energy is performed by an external device.

5. A method as in claim 4, wherein both the controlled vibrational energy and the electrical energy are delivered by an external device.

6. A method as in any one of claims 2–3, wherein the device is implanted at least partially under the patient's ribs.

7. A method as in any one of claims 2–3, wherein the device is implanted at least partially in a gap between the patient's ribs.

8. A method as in any one of claims 2–3, wherein the device is implanted at least partially over the patient's ribs.

9. A method as in any one of claims 2–3, wherein the device is implanted in the abdominal region.

10. A method as in any one of claims 2–3, wherein the device is implanted in the subcutaneous space of the anterior chest over the sternum.

11. A method as in any one of claims 2–3, wherein the device is implanted in a subcutaneous space of the anterior chest over the ribs.

12. A method as in any one of claims 2–3, wherein the device is implanted in a subcutaneous space of the posterior chest.

13. A method as in any one of claims 1–3, wherein delivering the vibrational energy comprises sequentially energizing individual vibrational transducer segments, wherein at least some of the segments direct vibrational energy to different regions of the heart.

14. A method as in any one of claims 1–3, wherein delivering vibrational energy comprises sequentially energizing individual vibrational transducer segments, wherein at least some of the segments direct vibrational energy to the same region of the heart.

15. A method as in any one of claims 1–3, wherein the vibrational transducer consists essentially of a single piezo-electric disposed in a housing with an air backing.

16. A method as in any one of claims 1–3, wherein the vibrational transducer comprises a piezo-composite material including piezo-electric ceramic posts in a polymer matrix.

17. A method as in any one of claims 1–3, wherein the vibrational energy has a frequency in the range from 0.02 to 10 MHz, a burst length less than 5,000 cycles, a burst rate less than 100 kHz, a duty cycle less than 50%, a mechanical index less than 50, and a thermal index less than 4.

18. A method as in any one of claims 1–3, wherein the vibrational energy is delivered to at least 50% of the heart.

19. A method as in any one of claims 1–3, wherein the vibrational energy is delivered to less than 50% of the heart.

20. A method as in claim 1, wherein the electrical energy is delivered externally at 360 Joules and below.

21. A method as in claim 1, wherein the electrical energy is delivered externally at 0.10 Joule and above.

22. A method as in claim 1, wherein the electrical energy is delivered through electrodes implanted in the heart, wherein the electrical energy is at 75 Joules and below.

23. A method as in claim 1, wherein the electrical energy is delivered through electrodes implanted in the heart, wherein the electrical energy is at 100 µJoules and above.

24. A method as in claim 1, wherein the electrical energy is delivered through electrodes implanted subcutaneously; wherein the electrical energy is at 75 Joules and below.

25. A method as in claim 1, wherein the electrical energy is delivered through electrodes implanted subcutaneously, wherein the electrical energy is at 100 µJoules and above.

26. A method as in any one of claims 1–3, further comprising detecting an onset of an arrhythmia in a patient and initiating at least one of delivering the controlled vibrational energy and the electrical energy automatically in response to such detection.

27. A method as in claim 26, wherein the deliveries of both the controlled vibrational energy and the electrical energy are initiated in response to detection of the arrhythmia.

28. A method as in any one of claim 1–3, wherein the delivery of at least one of the controlled vibrational energy and electrical energy is initiated manually.

29. A method as in claim 28, wherein the deliveries of both the controlled vibrational energy and the electrical energy are initiated manually.

30. A method as in any one of claims 1–3, wherein the vibrational energy is preferentially delivered to a ventricular region of the heart.

31. A method as in claim 29, wherein the electrical energy is preferentially delivered to a ventricular region of the heart.

32. A method as in any one of claims 1–3, wherein the vibrational energy is preferentially delivered to an atrial region of the heart.

33. A method as in claim 31, wherein the electrical energy is preferentially delivered to an atrial region of the heart.

34. A system for stabilizing cardiac arrhythmias, said system comprising:
    a vibrational transducer adapted to deliver vibrational energy to the heart while not in contact with the heart;
    electrical contacts adapted to deliver electrical energy to the heart; and
    control circuitry for delivering at least one of the vibrational energy and the electrical energy, wherein the control circuitry delivers the vibrational energy and the electrical energy at least partly simultaneously.

35. A system as in claim 34, wherein the system is implantable and the electrical contacts are adapted to directly engage the heart.

36. A system as in claim 34, wherein the system is implantable and the electrical contacts are adapted to indirectly engage the heart.

37. A system as in claim 34 or 35, wherein the vibrational transducer operates at a frequency in the range from 0.02 to 10 MHz, a burst length less than 5,000 cycles, a burst rate less than 100 kHz, a duty cycle less than 50%, a mechanical index less than 50, and a thermal index less than 4.

38. A system as in claims 34 or 35, wherein the control circuitry delivers electrical energy at 75 Joules and below.

39. A system as in claims 34 or 35, wherein the control circuitry delivers electrical energy at 100 µJoules and above.

40. A system as in claim 34, wherein the vibrational transducer and the electrical contacts are adapted to externally engage a surface of the patient's skin.

41. A system as in claim 34 or 40, wherein the vibrational transducer operates at a frequency in the range from 0.02 to 10 MHz, a burst length less than 5,000 cycles, a burst rate less than 100 kHz, a duty cycle less than 50%, a mechanical index less than 50, and a thermal index less than 4.

42. A system as in claim 41, wherein the control circuitry delivers electrical energy at 360 Joules and below.

43. A system as in claim 42, wherein the control circuitry delivers electrical energy at 0.10 Joule and above.

44. A system as in claim 34, wherein the control circuitry detects an onset of an arrhythmia and activates the vibrational transducer and delivers electrical energy in response to such detection.

45. A system as in claim 34, wherein the control circuitry is manually triggered to activate the vibrational transducer and deliver the electrical energy.

46. A system as in claim 34, wherein the delivery of vibrational energy is commenced prior to commencing the delivery of electrical energy.

47. A system as in claim 34, wherein the delivery of electrical energy is commenced prior to commencing the delivery of vibrational energy.

48. A system as in claim 34, wherein the vibrational transducer and the control circuitry are packaged in a common implantable housing.

49. A system as in claim 34, wherein the electrical contacts are adapted to form a part of the exterior of a common housing.

50. A system as in claim 34, wherein the electrical contacts comprise subcutaneously implantable leads.

51. A system as in claim 34, wherein the electrical contacts comprise transvenously implantable leads.

52. A system as in claim 34, wherein the vibrational transducer, the electrical contacts, and/or the control circuitry are packaged in separately implantable housings, further comprising cables for connecting the housings.

53. A system as in claim 34, wherein the vibrational transducer consists essentially of a single piezo-electric disposed in a housing with an air backing.

54. A system as in claim 34, wherein the vibrational transducer comprises a piezo-composite material including piezo-electric ceramic posts in a polymer matrix.

55. A system as in claim 34, wherein the vibrational transducer comprises a plurality of separately driven segments, wherein the segments are arranged to sequentially direct vibrational energy to different regions of the heart when the system is implanted.

56. A system as in claim 34, wherein the vibrational transducer comprises a plurality of separately driven segments, wherein the segments are arranged to sequentially direct vibrational energy to the same region of the heart when the system is implanted.

57. A system as in claim 34, wherein the vibrational transducer is adapted to preferentially deliver vibrational energy to a ventricular heart region when implanted.

58. A system as in claim 34, wherein the vibrational transducer is adapted to preferentially deliver vibrational energy, to an atrial region of the heart when implanted.

59. A system as in claim 34, wherein the control circuitry comprises sensor elements for detecting onset of an arrhythmia and for synchronizing the delivery of vibrational and electrical energy in response to such detection.

60. A system as in claim 59, wherein the control circuitry further comprises a power amplifier, an impedance matching circuit, and a signal generator, for each segment of the vibrational transducer.

61. A system as in claim 60, wherein the control circuitry further comprises a battery or a remotely rechargeable battery.

62. A system as in claim 61, wherein the control circuitry further comprises a transmitter and/or receiver for communication with an external controller.

* * * * *